United States Patent [19]

Aya et al.

[11] 4,029,646

[45] June 14, 1977

[54] BENZYL N,N-HEXAMETHYLENETHIOLCARBAMATE COMPOUNDS AND HERBICIDAL COMPOSITIONS

[75] Inventors: Masahiro Aya; Masao Miyamoto; Nobuo Fukazawa; Masaaki Yamagishi, all of Tokyo, Japan

[73] Assignee: Bayer Aktiengesellschaft, Leverkusen, Germany

[22] Filed: Feb. 9, 1971

[21] Appl. No.: 114,031

[30] Foreign Application Priority Data

Feb. 14, 1970 Japan .............................. 50-12463

[52] U.S. Cl. .............................. 260/239 BF; 71/88
[51] Int. Cl.$^2$ ........................................ C07D 295/10
[58] Field of Search ................... 260/239 BF; 71/88

[56] References Cited

UNITED STATES PATENTS

| | | | |
|---|---|---|---|
| 3,109,006 | 10/1963 | Harman et al. | 260/293.73 |
| 3,224,861 | 12/1965 | D'Amico | 260/239 BF |
| 3,303,014 | 2/1967 | D'Amico | 260/239 BF |

Primary Examiner—Raymond V. Rush
Attorney, Agent, or Firm—Burgess, Dinklage & Sprung

[57] ABSTRACT

Certain thiolcarbamate compounds of the general formula

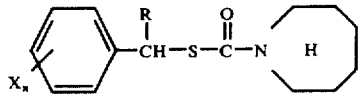

wherein
X is alkyl, e.g., lower alkyl, e.g., of from 1 to 4 carbon atoms, lower alkoxy of from, e.g., 1 to 3 carbon atoms, or halogen, e.g., chlorine or bromine, preferably chlorine. When n is greater than 1, the various radicals X may be the same or different, with provisos.
R is hydrogen, or methyl; and
n is an integer from 0 to 3;
are outstandingly effective herbicides, especially selective herbicides that can be used in rice paddies.

23 Claims, No Drawings

4,029,646

BENZYL N,N-HEXAMETHYLENETHIOLCARBAMATE COMPOUNDS AND HERBICIDAL COMPOSITIONS

The present invention relates to certain new thiolcarbamic acid ester compounds, to herbicidal compositions containing them, and to their use as herbicides, particularly as rice weed herbicides.

Pentachlorophenol (PCP) has been widely used to control *Echinochloa crus-galli*; (a weed growing in rice paddy fields: barnyard grass). Unfortunately. PCP has serious disadvantages: it has an inflammatry effect on the skin and mucous membranes of the human body and specific toxicity to fish and shellfish; it is also difficult to formulate. Another herbicide, 2-methyl-4-chlorophenoxyacetic acid (MCP), has been used to control the weed *Eleochalis acicularis* (spikerush) which grows in the same places. However, MCP does not adequately control barnyard grass.

French patent No. 1,328,112 discloses the weed-killing effects of benzyl-N,N-dialkylthiolcarbamic acid esters. U.S. Pat. No. 3,224,861 indicates that weed-killing properties are exhibited by thiol (or dithio) carbamic acid esters of the general formula:-

$$Y-Z-\overset{Z'}{\underset{\|}{C}}-N(CH_2)_4 \quad (II)$$

(wherein Z and Z' are oxygen or sulfur, and Y is a 1–4 halogen-substituted benzyl group).

U.S. Pat. No. 3,303,014 teaches that herbicidal activity is exhibited by benzylthiolcarbamic acid esters of the following general formula:-

$$\text{Ph}-CH_2-S-\overset{O}{\underset{\|}{C}}-N\overset{CH_2}{\underset{CH_2}{\diagdown}}(CH_2)_m \quad (III)$$

(wherein *m* is 4, 5 or 6).

In accordance with the present invention, it has surprisingly been found that the certain new substituted-benzyl-N,N-hexamethylenethiolcarbamate compounds are excellent herbicides and are especially effective against weeds in paddy fields, such as barnyard grass, spikerush and broad leaved weed.

Thus, the compounds of the present invention exhibit very strong weed-killing effects on *Panicum crusgalli* in the irriguous treatment at the pre-emergence stage and the first to third leaf stage, and moreover are characterized by less toxicity against rice plants when compared with the convential benzylthiolcarbamates. The foregoing effect is most significant since most of the known commercially available herbicides are effective against barnyard grass only during the pre-or just post-emergence period thereof.

Furthermore, because they are less phytotoxic to rice plants, the compounds of the present invention can effectively control various weeds in rice cultivation when applied during a period in which it has hitherto not been possible to apply effective control, that is one to two weeks after transplantation of the rice. The compounds are useful also in decreasing the labour needed in cultivation.

Another advantage of the compounds of the present invention is that they are effective as non-selective herbicides against some weeds other than the foregoing weeds in paddy field, especially when applied by soil treatment before germination thereof, as they are well absorbed by these weeds from the root.

The present invention provides thiolcarbamic acid ester $$X_n\text{-Ph-}\underset{R}{\overset{|}{CH}}-S-\underset{\|}{\overset{O}{C}}-N(\text{hexamethylene})H \quad (I)$$

wherein

X is alkyl, e.g., lower alkyl, e.g., of from 1 to 4 carbon atoms, lower alkoxy of from, e.g., 1 to 3 carbon atoms, or halogen, e.g., chlorine or bromine, preferably chlorine. When n is greater than 1, the various radicals X may be the same or different.

R is hydrogen, or methyl; and n is an integer from 0 to 3; with the proviso that when R is hydrogen, n is from 1 to 3, and at least one of X is alkyl or alkoxy; or with the alternative proviso that when R is hydrogen and X is halogen then n is 1 and its substituted position is para.

The invention also provides a process for the production of a compound of the formula (I) in which a. a benzyl mercaptan of the general formula:

$$X_n\text{-Ph-}\underset{R}{\overset{|}{CH}}-SM' \quad (IV)$$

is reacted with a N,N-hexamethylene carbamoyl halide of the general formula:

$$Hal-\overset{O}{\underset{\|}{C}}-N(\text{hexamethylene})H \quad (V)$$

or b. a benxylthiocarbonyl halide of the general formula:

$$X_n\text{-Ph-}\underset{R}{\overset{|}{CH}}-S-\overset{O}{\underset{\|}{C}}-Hal \quad (VI)$$

is reacted with N,N-hexamethyleneimine of the formula:

$$HN(\text{hexamethylene})H \quad (VII)$$

or c. a benzyl halide of the general formula:

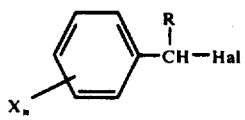

is reacted with the compound of the formula (VII) and carbonyl sulfide of the formula:

COS (IX)

wherein X, R and $n$ have the same meanings as in formula (I), M' is hydrogen or a metal equivalent and Hal is halogen. Process variant (a) is illustrated by the following reaction scheme:

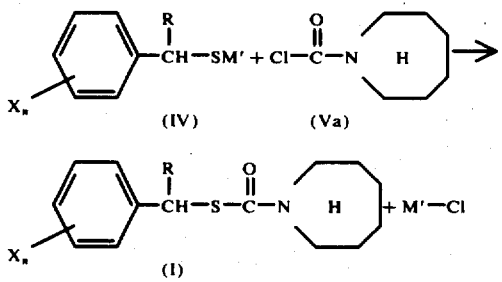

Examples of substituted benzyl mercaptans of formula (IV) include 2-(3- or 4-)methylbenzyl-, 4-ethylbenzyl-, 4-n-(or iso-) propylbenzyl-, 4-n-(iso-, sec.- or tert.-)butylbenzyl-, 2,5-(or 3,4-)dimethylbenzyl-, 2-(3-or 4-)methoxybenzyl-, 4-ethoxybenzyl-, 4-n-(or iso-)propoxybenzyl-, 4-n-(iso-, sec.- or tert.-)butoxybenzyl-, 2-methoxy-5-chloro-(bromo- or methyl-)benzyl-, 4-methoxy-3-chloro-(bromo- or methyl-)benzyl-, 4-ethoxy-3-chloro-(bromo- or methyl-)benzyl-, 4-n-(or iso-)propoxy-3-chloro-(bromo- or methyl-)benzyl-, 4-methoxy-3,5-dichloro-benzyl-, 2,4,5-(or 2,4,6-) trichloro-benzyl-, α-methyl-benzyl-, α-methyl-2-(3-or 4-)chloro-benzyl-, α-methyl-2,4-(or 2,6-)dichloro-benzyl, α-methyl-2,4,5-(or 2,4,6-)trichloro-benzyl-, α-methyl-2-(3- or 4-)methyl-benzyl-, α-methyl-2,5-(or 3,4-)dimethyl-benzyl-, 2-(3- or 4-)methoxy-benzyl-, α-methyl-2-methoxy-5-chloro-(bromo- or methyl-)benzyl-and α-methyl-4-methoxy(or iso-propoxy)-3-chloro-(bromo- or methyl-) benzyl- mercaptan and the alkali metal salts thereof.

M' is preferably hydrogen or an alkali metal such as sodium, potassium or lithium; most preferably, it is hydrogen or sodium.

In all three process variants, the reaction may be carried out in the presence of a solvent (this term includes a mere diluent).

For this purpose, there may be used aliphatic or aromatic hydrocarbons (optionally halogenated), for example benzine, methylene chloride, chloroform, carbon tetrachloride, benzene, chlorobenzene, toluene or xylene; ethers, for example diethyl ether, dibutyl ether, dioxan or tetrahydrofuran; lower boiling alcohols, for example methanol, ethanol or isopropanol; and ketones, for example acetone, methyl ethyl ketone, methyl isopropyl ketone or methyl isobutyl ketone. Also lower aliphatic nitriles, for example acetonitrile or propionitrile, can be used.

The reaction may be conducted, if necessary, in the presence of an acid-binding agent. For the purpose, there may be used carbonates and bicarbonates of alkali metals, for example sodium bicarbonate, potassium carbonate or sodium carbonate alcoholates of alkali metals, for example potassium methylate or ethylate and aliphatic, aromatic or heterocyclic tertiary bases, for example triethylamine, diethylamine and psyridine.

Process variant (b) is illustrated by the following reaction scheme:

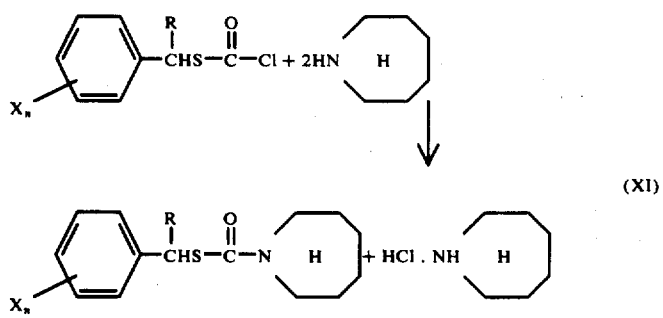

(XI)

Examples of the benzylthiocarbonyl halides of the general formula (V) include 2-(3- or 4-)methylbenzyl-, 4-ethylbenzyl-, 4-n-(or iso-) propylbenzyl-, 4-n-(iso-, sec.- or tert.-)butylbenzyl-, 2,5-(or 3,4-)dimethylbenzyl-, 2-(3-or 4-)methoxybenzyl-, 4-ethoxybenzyl-, 4-n-(or iso-)propoxybenzyl-, 4-n-(iso-, sec.- or tert.-)butoxy-benzyl-, 2-methoxy-5-chloro-(bromo- or methyl-)benzyl-, 4-methoxy-3-chloro-(bromo- or methyl-)benzyl-, 4-ethoxy-3-chloro-(bromo- or methyl-)benzyl-, 4-n-(or iso-)propoxy-3-chloro-(bromo- or methyl-)benzyl-, 4-methoxy-3,5-dichloro-benzyl-, 2,4,5-(or 2,4,6-) trichloro-benzyl-, α-methyl-benzyl-, α-methyl-2-(3-or 4-)chlorobenzyl-, α-methyl-2,4-(or 2,6-)dichloro-benzyl, α-methyl-2,4,5-(or 2,4,6-)trichloro-benzyl-, α-methyl-2-(3- or 4)methyl-benzyl-, α-methyl-2,5-(or 3,4-)dimethyl-benzyl-, 2-(3- or 4-)methoxy- benzyl-, α-methyl-2-methoxy-5-chloro-(bromo- or methyl-)benzyl- and α-methyl-4-methoxy (or iso-propoxy)-3-chloro-(bromo- or methyl-) benzyl-thiocarbonyl chloride.

Process variant (c) is illustrated by the following formula scheme:

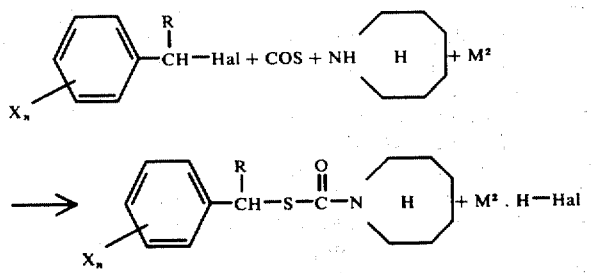

(XII)

wherein
$M^2$ is an alkali.

The compounds of the present invention are superior in weed-controlling activity to the most known compounds having analogous structures.

The compounds can have either a total herbicidal effect or a selective herbicidal effect, depending on the amount used. Larger amounts, for example 5 to 40 kg of active compound per hectare, generally have a total herbicidal effect, while smaller amounts, for example 1.25 to 5 kg of active compound per hectare, generally have a selective effect.

The compounds according to the present invention can be effectively used as germination-controlling agents, especially weed-controlling agents.

The term weed used herein is intended to cover broadly practically all plants growing in undesirable places. In particular, the compounds according to the present invention are active against the following plants and exhibit excellent selective weed-killing or withering effects when used in the proper quantity (for example, 1.25 to 5kg per hectare), and can be especially desirably used as herbicides for those crops, marked with an asterisk (*), below, in fields or paddies.

| Plant name | Latin name |
| --- | --- |
| Dicotyledons | |
| Mustard | Sinapis |
| Rape | Lepidium |
| Catch weed | Galium |
| Chickweed | Stellaria |
| Sweet false | Matricaria |
| French weed | Galinsoga |
| Goosefoot | Chenopodium |
| Nettle | Urtica |
| Groundsel | Senecio |
| Tampala | Amaranthus |
| Purslane | Portulaca |
| Cotton | Gossypium |
| Carrot | Daucus |
| Pulse | Phaseolus |
| Potato | Solanum |
| Coffee | Coffea |
| Beet | Beta |
| Cabbage | Brassica |
| Spinach | Spinacia |
| Monocotyledons | |
| Timothy | Phleum |
| Eragrostis niwahokori Honda | Poe |
| Festuca parvigluma | Festuca |
| Finger-grass | Digitaria |
| Goose grass | Eleusine |
| Foxtail | Setaria |
| Ray grass | Bromus |
| Barn yard grass | Echinochlora |
| Maize | Zea |
| Rice plant | Oryza |
| Oats | Avena |
| Barley | Hordeum |
| Wheat | Tritium |
| Millet | Panicum |
| Sugar cane | Saccharum |

The species of the above plants are considered to be typical examples of the genus identified by the Latin name. The applicability of the active compounds according to the present invention is, of course, not limited to these plants and they are effective for other analogous plants.

The active compounds according to the present invention can be converted into the usual formulations, such as solutions, emulsions, suspensions, powders, pastes and granulates. These may be produced in known manner, for example by mixing the active compounds with extenders, that is, liquid or solid or gaseous diluents or carriers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene, dimethyl naphthalene or aromatic naphthas chlorinated aromatic or aliphatic hydrocarbons, such as chlorobenzenes, chloromethylene, chloroethalene or carbon tetrachloride, aliphatic hydrocarbons, such as cyclohexane or paraffins (for example mineral oil fractions), alcohols, such as methanol or butanol, ketones such as acetone, methyl ethyl ketone or cyclohexanone, or strongly polar solvents, such as dimethyl formamide, dimethyl sulfoxide or acetonitrile, as well as water.

As solid diluents or carriers, there are preferably used ground natural minerals, such as kaolins, clays, talc, chalk, attapulgite, montmorillonite or diatomaceous earth or ground synthetic minerals, such as highly-dispersed silicic acid, alumina or silicates.

As gaseous diluents or carriers there may be used aerosol propellants which are gaseous at normal temperatures and pressures, such as freon.

Preferred examples of emulsifying agents include non-ionic and anionic emulsifiers, such as polyoxyethylene-fatty acid esters, polyoxyethylene-fatty alcohol ethers, for example alkylarylpolyglycol ethers, alkyl sulfonates and aryl sulfonates; and preferred examples of dispersing agents include lignin, sulfite waste liquors and methyl cellulose.

The compounds of the present invention can be used, if desired, together with other agricultural chemicals, for example insecticides, nematicides, fungicides (including antibiotics), herbicides, plant growth-regulators or fertilizers.

The herbicidal, miticidal and fungicidal composition according to the present invention generally contains 0.1 to 95 percent by weight, preferably 0.5 to 90% by weight, of the active compound. However, the content of active ingredients may be varied in accordance with the formulation and the applying method, the purpose, the period of application, the place of application and other circumstances.

The compounds may be formulated in any of the usual ways in the field of agricultural chemicals, for example solutions, emulsions, emulsion concentrates, wettable powders, aqueous solutions, oil formulations, aerosols, pastes, fumigants, dusting powders, coating granules, tablets, granules, pellets and the like.

The compounds may be applied to the pest or its habitat in any of the usual ways, for example, by scattering, spraying, atomizing, misting, dusting, mixing, fumigating, injecting or powder-coating methods.

Furthermore, the application can be effected by the so-called "ultra-low-volume" method. In this method it may be possible to use 95 to 100% of the active compound.

In use, the content of the active ingredient in the ready-to-use preparation can be varied over a broad range according to circumstances. However, it may generally be preferable to use a range from 0.001 to 20% by weight, especially 0.005 to 5.0% by weight.

Also, the amount of active compound applied per unit area is usually about 15 to 2000 grams, preferably 40 to 1000 grams of active compound per 10 acres. However, in special cases, it may be possible to use more or less sometimes such variations may be required.

The invention therefore provides a herbicidal, acaricidal or fungicidal composition containing as active ingredient a compound according to the invention in admixture with a solid diluent or carrier or in admixture with a liquid diluent or carrier containing a surface-active agent.

The invention also provides a method of combating weeds, acarids or fungi which comprises applying to these pests or a habitat thereof a compound according to the invention alone or in the form of a composition containing as active ingredient a compound according to the invention in admixture with a solid or liquid diluent or carrier.

The invention also provides crops protected from damage by seeds, acarids or fungi by being grown in areas in areas in which, immediately prior to and/or during the time of the growing, a compound according to the invention was applied alone or in admixture with a solid or liquid diluent or carrier. It will be seen that the usual methods of providing harvested crops may be improved by the present invention.

The invention is illustrated by the following Examples. In all the Examples, the numbers of the compounds correspond to those in Table 1, infra.

EXAMPLE 1

Preparation of 3-chloro-4-methoxybenzyl-N,N-hexamethylenethiolcarbamate

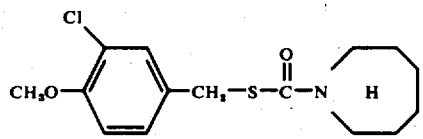

(8)

To a solution of 18.9 g (0.1 mole) of 3-chloro-4-methoxy-benzyl mercaptan in 200 ml of acetone were added gradually 10 ml of 40% aqueous caustic soda solution to make the sodium salt of 3-chloro-4-methoxybenzyl mercaptan. 16g (0.1 mole) of N,N-hexamethylene carbamoyl chloride were gradually added dropwise thereto at 10° – 20° C.

After completion of the addition, the reaction was completed by stirring for 3 to 4 hours at room temperature. Then the sodium chloride by-produced was filtered off, the acetone was distilled off and cold water was added to obtain the desired compound in the form of crude crystal.

Furthermore, by recrystallizing it from ethanol, 27.4 g of white crystals of 3-chloro-4-methoxybenzyl-N,N-hexamethylenethiolcarbamate were obtained.

Yield: 87.3%. m.p. 64°–65° C

EXAMPLE 2

Preparation of 2,5-dimethylbenzyl-N,N-hexamethylenethiolcarbamate

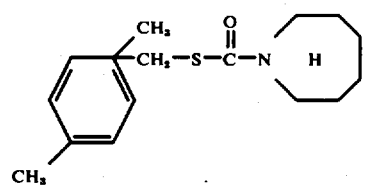

(5)

A dilution of 21.5 g (0.1 mole) of 2,5-dimethylbenzylthiocarbonyl chloride (b.p.: 85°–87° C/0.05 mmHg) in 200 ml of ether was cooled to 0°–5° C, and a solution of 19.8 g (0.2 mole) of N,N-hexamethyleneimine in 100 ml of ether was gradually added dropwise thereto with stirring. After the addition had ended, the reaction was continued for an additional hour and the reaction mixture was allowed to stand for 12 hours at room temperature. The amine salt precipitated was filtered off, and the ethereal layer was washed with 1% caustic soda solution, with 1% hydrochloric acid solution and with water, and was thereafter dried over anhydrous sodium sulphate.

After distilling off the ether, the residue was distilled umder reduced pressure to obtain 24.0 g of 2,5-dimethylbenzyl-N,N-hexamethylenethiolcarbamate.

Yield: 86.6%. b.p. 165°–170° C/0.1 mmHg)

EXAMPLE 3

Preparation of α-methylbenzyl-N,N-hexamethylenethiolcarbamate

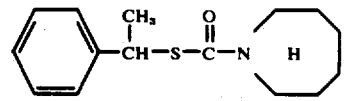

(21)

A solution of 20.0 g (0.1 mole) of α-methylbenzylthiocarbonyl chloride (b.p.: 72°–74° C/0.15 mm Hg) in 200 ml of ether was cooled to 0°–5° C, and a solution of 19.8 g (0.2 mole) of N,N-hexamethyleneimine in 100 ml of ether was gradually added dropwise thereto with stirring.

After the addition had ended, the reaction was continued for an additional hour and the reaction mixture was allowed to stand for 12 hours at room temperature. The amine salt precipitated was filtered off, and the ethereal layer was washed with 1% caustic soda solution, with 1% hydrochloric acid solution and with water, and was thereafter dried over anhydrous sodium sulphate. After distilling off the ether, the residue was distilled under reduced pressure to obtain 22 g of α-methylbenzyl-N,N-hexamethylene-thiolcarbamate (racemic compound).

Yield: 83.6%, b.p.: 152°–160° C/0.1 mm Hg.

Typical examples of the compounds of the present invention, synthesized by methods analogous to those of Examples 1 to 3, are listing in the following Table 1. The table gives the boiling points or (in brackets) the melting points of the compounds. In some cases it also gives the refractive indices.

Table 1

| Compound | Chemical Name | Structure | b.p.° C/mm Hg or [m.p. °C] | Refractive index $n_D^{20}$ |
|---|---|---|---|---|
| (1) | 4-methylbenzyl N,N-hexamethylene-thiolcarbamate | 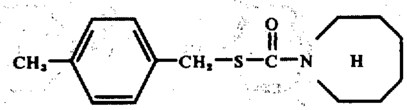 | 146–152/0.1 | 1.5754 |
| (2) | 4-ethylbenzyl N,N-hexamethylene-thiolcarbamate | 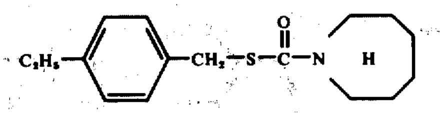 | 157–165/0.2 | 1.5710 |
| (3) | 4-iso-propylbenzyl N,N-hexamethylene-thiolcarbamate | 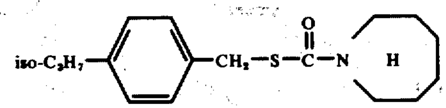 | 160–166/0.2 | 1.5624 |
| (4) | 4-tert-butylbenzyl N,N-hexamethylene-thiolcarbamate | 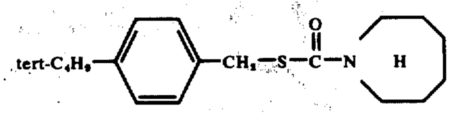 | 173–177/0.2 | 1.5592 |
| (5) | 2,5-dimethylbenzyl N,N-hexamethylene-thiolcarbamate | 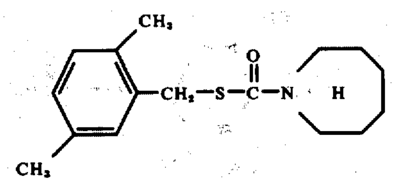 | 165–170/0.1 | 1.5717 |
| (6) | 3,4-dimethylbenzyl N,N-hexamethylene-thiolcarbamate | 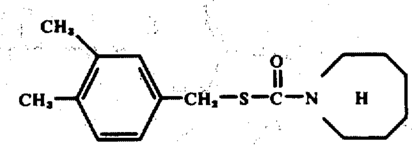 | 164–169/0.3 | 1.5730 |
| (7) | 4-methoxybenzyl N,N-hexamethylene-thiolcarbamate | 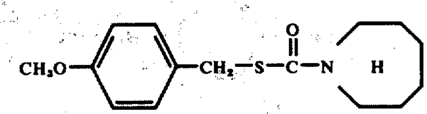 | 177–182/0.1 | 1.5752 |
| (8) | 3-chloro-4-methoxybenzyl N,N-hexamethylene-thiolcarbamate | 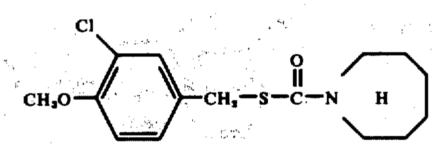 | (64–65) | |
| (9) | 3-chloro-4-ethoxybenzyl N,N-hexamethylene-thiolcarbamate | 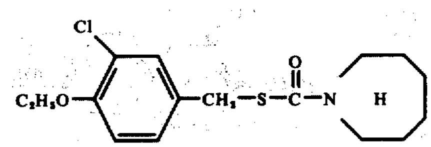 | (60–61) | |
| (10) | 3-chloro-4-isopropoxybenzyl N,N-hexamethylene-thiolcarbamate | 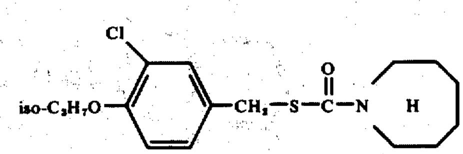 | (51–52) | |

Table 1-continued

| Compound | Chemical Name | Structure | b.p.° C/mm Hg or [m.p. ° C] | Refractive index $n_D^{20}$ |
|---|---|---|---|---|
| (11) | 3-bromo-4-methoxybenzyl N,N-hexamethylene-thiolcarbamate | 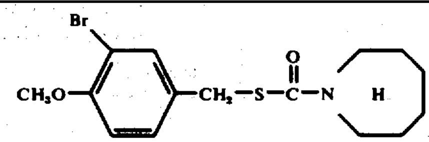 | 207–210/0.5 | 1.5989 |
| (12) | 2-methoxy-5-chlorobenzyl N,N-hexamethylene-thiolcarbamate | 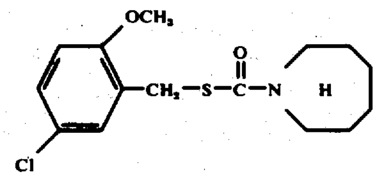 | 185–192/0.15 | 1.5839 |
| (13) | 2-methoxy-5-methylbenzyl N,N-hexamethylene-thiolcarbamate | 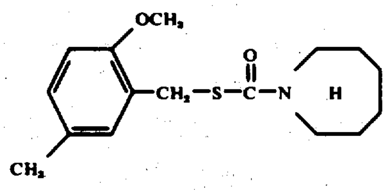 | 177–181/0.2 | 1.5749 |
| (14) | 2-methoxy-5-bromobenzyl N,N-hexamethylene-thiolcarbamate | 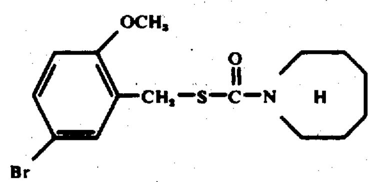 | 200–205/0.7 | 1.5920 |
| (15) | 3-methyl-4-ethoxybenzyl N,N-hexamethylene-thiolcarbamate | 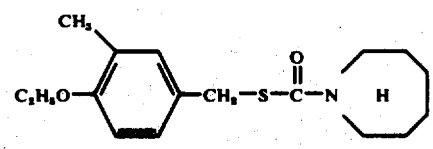 | 175–180/0.25 | 1.5648 |
| (16) | 3-methyl-4-isopropoxybenzyl N,N-hexamethylene-thiolcarbamate | 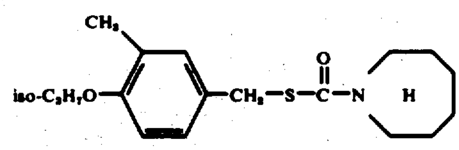 | (62–63) | |
| (17) | 3,5-dichloro-4-methoxybenzyl N,N-hexamethylene-thiolcarbamate | 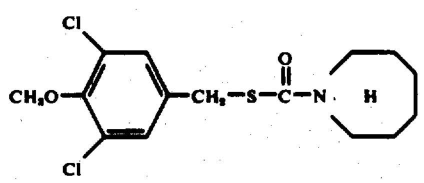 | (60–62) | |
| (18) | 3-methyl-4-methoxybenzyl N,N-hexamethylene-thiolcarbamate | 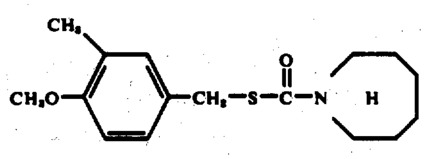 | 188–190/1.0 | 1.5731 |
| (19) | 3-chloro-4-n-propoxybenzyl N,N-hexamethylene-thiolcarbamate | 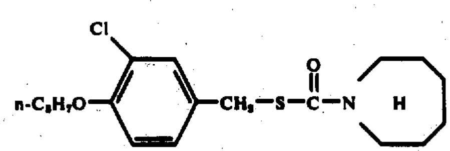 | (46–47) | |
| (20) | 2,4,5-trichlorobenzyl N,N-hexamethylene-thiolcarbamate | 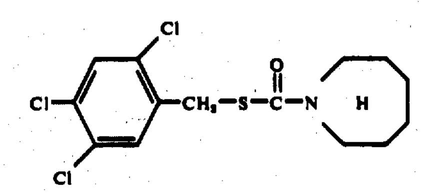 | 182–186/0.5 | 1.5720 |

Table 1-continued

| Compound | Chemical Name | Structure | b.p. °C/mm Hg or [m.p. °C] | Refractive index $n_D^{20}$ |
|---|---|---|---|---|
| (21) | α-methylbenzyl N,N-hexamethylene-thiolcarbamate | (structure) | 152–160/0.1 | 1.5700 |
| (22) | α-methyl-2-chlorobenzyl N,N-hexamethylene-thiolcarbamate | (structure) | 155–156/0.1 | 1.5750 |
| (23) | α-methyl-4-chlorobenzyl N,N-hexamethylene-thiolcarbamate | (structure) | 159–165/0.4 | 1.5759 |
| (24) | α-methyl-4-methoxybenzyl N,N-hexamethylene-thiolcarbamate | (structure) | 163–166/0.1 | 1.5713 |
| (25) | 4-ethoxybenzyl-N,N-hexamethylenethiol-carbamate | (structure) | 186–191/0.4 | 1.5688 |
| (26) | 4-isopropoxybenzyl-N,N-hexamethylene-thiolcarbamate | (structure) | (49–51) | |

In bio-testing these compounds, they were formulated conventionally as illustrated by the following examples:

EXAMPLE (i)

5% of Compound (1) of Table 1 and 95% of a mixture of talc and clay were crushed and mixed to prepare a dusting powder (Dust). In use, the dust may be directly applied, [talc and clay (3:1); The term (%) used in the Example (i) to (iv) means weight.]

EXAMPLE (ii)

20% of Compound (2) of Table 1, 75% of a mixture of talc and clay, 3% of sodium alkyl benzene sulphonate and 2% of sodium dinaphthylemethane disulphonate were crushed and mixed to prepare a wettable powder. The powder can be used after being diluted with water. [talc and clay (3:2)]

EXAMPLE (iii)

20% of Compound (5) of Table 1, 75% of xylol and 5% of the emulsifier Sorpol (Trade Mark) were mixed to prepare an emulsion concentrate. The concentrate can be applied after being diluted with water. (Sorpol: polyoxyethylenealkylarylether)

EXAMPLE (iv)

Compound (8) of Table 1 was heat-dissolved in xylol, and the solution was sprayed on to clay granules so that they contained about 10% of the active ingredient. The resulting granules can be directly scattered on the soil surface.

When compared with known active compounds having analogous structure and a similar direction of activity, the new substituted-benzyl-N,N-hexamethylenethiolcarbamates of the present invention are characterized by substantially improved effects, decreased phytotoxicity to useful crops and much lower toxicity to warm blooded animals. The new compounds are therefore very useful.

EXAMPLE A

Pre-emergence soil-treating test for weeds in paddy field under irrigation (Pot test):
Solvent: 5 parts by weight of acetone
Emulsifier: 1 part by weight of benzyloxypolyglycol ether
The active compound was incorporated into an emulsifiable concentrated by mixing 1 part by weight thereof with said solvent and the stated amounts of the emulsifier. The preparation thus obtained was diluted with water.

Test method:

A 1/5,000 are Wagner pot was charged with paddy field soil, and a rice plant seedling (Kinmaze variety) during the 3rd to the 4th leaf stage was transplanted into the pot.

After rooting of the seedling, seeds of barnyard grass and a broad-leaved weed were sown, and spikerush was transplanted into the pot.

The said preparation of active compound was applied into the pot in a dosage of 500, 250 or 125 g of active compound per 10 ares. The damage degree of the weeds to be tested after 4 weeks were evaluated on a scale from 0 to 5, the scale values having the following meanings. The degree of phytotoxicity was also determined in accordance with the second scale below. The term "a 1/5,000 are Wagner pot" means a pot which covers a space of 0.02 m².

Degree of damage
5: Weed-killing as compared with untreated plot — over 95% (withering)
4: " — over 80%
3: " — over 50%
2: " — over 30%
1: " — over 10%
0: " — below 10% (not effective)

Degree of phytotoxicity:
5: Phytotoxicity as compared with untreated plot — over 90% (mortal damage)
4: Phytotoxicity rate to untreated plot — over 50%
3: " — over 30%
2: " — below 30%
1: " — below 10%
0: " — 0% (no phytotoxicity)

The test results are given in Table 2.

Table 2

| Compound No. | Content of active ingredient (g/10 ares) | Degree of damage ECHC | Degree of damage ELOA | Degree of damage Broad-leaved weed | Phytotoxicity Rice plant |
|---|---|---|---|---|---|
| (1) | 500 | 5 | 5 | 5 | 0 |
|  | 250 | 5 | 5 | 5 | 0 |
|  | 125 | 5 | 4–5 | 5 | 0 |
| (2) | 500 | 5 | 5 | 5 | 0 |
|  | 250 | 5 | 5 | 5 | 0 |
|  | 125 | 5 | 4–5 | 5 | 0 |
| (3) | 500 | 5 | 5 | 5 | 0 |
|  | 250 | 5 | 5 | 4–4 | 0 |
|  | 125 | 5 | 4 | 4 | 0 |
| (4) | 500 | 5 | 5 | 5 | 0 |
|  | 250 | 4–5 | 4–5 | 4 | 0 |
|  | 125 | 4 | 4 | 4 | 0 |
| (5) | 500 | 5 | 5 | 5 | 0 |
|  | 250 | 5 | 5 | 5 | 0 |
|  | 125 | 5 | 4–5 | 5 | 0 |
| (6) | 500 | 5 | 5 | 5 | 0 |
|  | 250 | 5 | 4 | 4 | 0 |
|  | 125 | 4 | 4 | 3 | 0 |
| (7) | 500 | 5 | 5 | 5 | 0 |
|  | 250 | 5 | 5 | 4–5 | 0 |
|  | 125 | 5 | 4 | 4 | 0 |
| (8) | 500 | 5 | 5 | 5 | 0 |
|  | 250 | 5 | 5 | 5 | 0 |
|  | 125 | 5 | 4–5 | 5 | 0 |
| (9) | 500 | 5 | 5 | 5 | 0 |
|  | 250 | 5 | 5 | 5 | 0 |
|  | 125 | 4–5 | 4–5 | 5 | 0 |
| (10) | 500 | 5 | 5 | 5 | 0 |
|  | 250 | 5 | 5 | 5 | 0 |
|  | 125 | 5 | 4–5 | 5 | 0 |
| (11) | 500 | 5 | 5 | 5 | 0 |
|  | 250 | 5 | 5 | 5 | 0 |
|  | 125 | 4–5 | 4–5 | 5 | 0 |
| (12) | 500 | 5 | 5 | 5 | 0 |
|  | 250 | 4–5 | 4 | 5 | 0 |
|  | 125 | 4 | 3–4 | 4 | 0 |
| (13) | 500 | 5 | 5 | 5 | 0 |
|  | 250 | 4–5 | 4 | 4–5 | 0 |
|  | 125 | 4 | 4 | 4–5 | 0 |
| (14) | 500 | 5 | 5 | 5 | 0 |
|  | 250 | 5 | 5 | 5 | 0 |
|  | 125 | 4 | 4–5 | 5 | 0 |
| (15) | 500 | 5 | 5 | 5 | 0 |
|  | 250 | 5 | 5 | 5 | 0 |
|  | 125 | 4 | 4–5 | 5 | 0 |
| (16) | 500 | 5 | 5 | 5 | 0 |
|  | 250 | 5 | 5 | 5 | 0 |
|  | 125 | 4–5 | 4–5 | 5 | 0 |
| (17) | 500 | 5 | 5 | 5 | 0 |
|  | 250 | 5 | 5 | 5 | 0 |
|  | 125 | 5 | 5 | 4–5 | 0 |
| (18) | 500 | 5 | 5 | 4–5 | 0 |
|  | 250 | 5 | 4 | 4 | 0 |
|  | 125 | 5 | 3 | 3 | 0 |
| (19) | 500 | 5 | 5 | 5 | 0 |
|  | 250 | 4 | 4 | 4 | 0 |
|  | 125 | 4 | 3–4 | 3–4 | 0 |
| (20) | 500 | 5 | 5 | 5 | 0 |
|  | 250 | 5 | 4 | 4 | 0 |
|  | 125 | 4 | 4 | 3–4 | 0 |

Table 2-continued

| Compound No. | Content of active ingredient (g/10 ares) | Degree of damage ECHC | Degree of damage ELOA | Degree of damage Broad-leaved weed | Phytotoxicity Rice plant |
|---|---|---|---|---|---|
| (21) | 500 | 5 | 5 | 5 | 0 |
|  | 250 | 4–5 | 4 | 5 | 0 |
|  | 125 | 4 | 3–4 | 4 | 0 |
| (22) | 500 | 5 | 5 | 5 | 0 |
|  | 250 | 4–5 | 4 | 4 | 0 |
|  | 125 | 3 | 3 | 3 | 0 |
| (23) | 500 | 5 | 5 | 5 | 0 |
|  | 250 | 4–5 | 4–5 | 4 | 0 |
|  | 125 | 3 | 3 | 3 | 0 |
| (24) | 500 | 5 | 5 | 5 | 0 |
|  | 250 | 4 | 4 | 4 | 0 |
|  | 125 | 3 | 3 | 3–4 | 0 |
| (25) | 500 | 5 | 5 | 5 | 0 |
|  | 250 | 5 | 5 | 4 | 0 |
|  | 125 | 4–5 | 4 | 4 | 0 |
| (26) | 500 | 5 | 5 | 5 | 0 |
|  | 250 | 5 | 4–5 | 4–5 | 0 |
|  | 125 | 5 | 4 | 4 | 0 |
| A (Comparison; French patent 1328112) | 500 | 5 | 5 | 5 | 4 |
|  | 250 | 5 | 4 | 4 | 2 |
|  | 125 | 4 | 3 | 3 | 1 |
| PCP (Commercial available comparison) | 800 | 4 | 0 | 4 | 0 |
|  | 600 | 0 | 0 | 0 | 0 |
| Untreated plot (control) | — | 0 | 0 | 0 | 0 |

1. Compound Nos. in the table are the same as in the preparative Examples and Table 1.
2. ECHC: Barnyard grass
3. ELOA: Spikerush
4. Broad-leaved weeds: Monochoria, Rotala indica, Koehne and False pimpernel, etc.
5. A: Benzyl-N,N-diethylthiolcarbamate
6. PCP: Pentachlorophenol

EXAMPLE B

Post-emergence soil-treating test for weeds in paddy field under irrigation (Pot test)

A 1/500 are Wagner pot was charged with a paddy field soil. and two rice plant seedlings (Kinmaze variety) during the 3rd to the 4th leaf stage were transplanted into the pot.

Seeds of barnyard grass and a broad-leaved weed were sown, and spikerush was transplanted into the pot.

The pot was put into an irrigating condition and when the barnyard grass had grown to about the 2nd leaf stage (on the 7 to 9th day after sowing), the pot was irrigated to about 6 cm in depth. Thereafter, the preparation of the active compound in the form of the same emulsion as in Example A was sprayed into the pot in a predetermined amount. After the treatment, the irrigation was discharged for 2 days at a rate of 2 to 3 cm per day, and maintained in a depth of about 3 cm.

The herbicidal effect (degree of damage to the weeds) and the phytotoxicity were determined 4 weeks after the application of the active compound and were evaluated in accordance with the scales given in Example 1.

The test results are given in Table 3.

Table 3

Test results

| Compound No. | Content of active ingredient (g/10 ares) | Degree of damage ECHC | Degree of damage ELOA | Degree of damage Broad-leaved weed | Phyto-toxicity Rice plant |
|---|---|---|---|---|---|
| (1) | 600 | 5 | 4–5 | 5 | 0 |
|  | 300 | 5 | 4 | 4 | 0 |
|  | 150 | 3 | 3 | 3 | 0 |
| (2) | 600 | 5 | 5 | 5 | 0 |
|  | 300 | 5 | 4 | 4 | 0 |
|  | 150 | 3–4 | 3–4 | 3 | 0 |
| (3) | 600 | 5 | 5 | 5 | 0 |
|  | 300 | 5 | 4 | 4 | 0 |
|  | 150 | 4 | 3 | 3 | 0 |
| (4) | 600 | 5 | 5 | 5 | 0 |
|  | 300 | 5 | 4 | 4 | 0 |
|  | 150 | 4 | 3 | 4 | 0 |
| (5) | 600 | 5 | 5 | 5 | 0 |
|  | 300 | 5 | 4–5 | 5 | 0 |
|  | 150 | 4–5 | 4–5 | 4 | 0 |
| (6) | 600 | 5 | 5 | 5 | 0 |
|  | 300 | 4 | 4–5 | 4 | 0 |
|  | 150 | 3 | 3–4 | 4 | 0 |
| (7) | 600 | 5 | 5 | 4 | 0 |
|  | 300 | 5 | 4 | 3 | 0 |
|  | 150 | 4 | 4 | 3 | 0 |
| (8) | 600 | 5 | 5 | 5 | 0 |
|  | 300 | 5 | 5 | 4–5 | 0 |
|  | 150 | 4–5 | 4–5 | 3 | 0 |
| (9) | 600 | 5 | 5 | 5 | 0 |
|  | 300 | 5 | 5 | 4–5 | 0 |
|  | 150 | 4–5 | 4–5 | 3–4 | 0 |
| (10) | 600 | 5 | 5 | 5 | 0 |
|  | 300 | 5 | 5 | 4–5 | 0 |
|  | 150 | 4–5 | 4–5 | 4 | 0 |
| (11) | 600 | 5 | 5 | 5 | 0 |
|  | 300 | 5 | 5 | 4–5 | 0 |
|  | 150 | 4–5 | 4 | 3 | 0 |
| (12) | 600 | 5 | 5 | 5 | 0 |
|  | 300 | 4 | 4 | 5 | 0 |
|  | 150 | 4 | 3 | 5 | 0 |
| (13) | 600 | 5 | 5 | 5 | 0 |
|  | 300 | 4 | 4 | 5 | 0 |
|  | 150 | 3–4 | 3 | 4–5 | 0 |
| (14) | 600 | 5 | 5 | 5 | 0 |
|  | 300 | 5 | 5 | 4–5 | 0 |
|  | 150 | 4 | 4 | 4 | 0 |
| (15) | 600 | 5 | 5 | 5 | 0 |
|  | 300 | 5 | 4–5 | 4 | 0 |
|  | 150 | 4 | 3 | 3–4 | 0 |
| (16) | 600 | 5 | 5 | 5 | 0 |
|  | 300 | 5 | 4–5 | 5 | 0 |
|  | 150 | 5 | 4 | 4 | 0 |
| (17) | 600 | 5 | 5 | 5 | 0 |
|  | 300 | 5 | 4–5 | 4 | 0 |
|  | 150 | 4–5 | 4 | 4 | 0 |
| (18) | 600 | 5 | 5 | 4–5 | 0 |
|  | 300 | 4 | 3 | 4 | 0 |
|  | 150 | 3 | 3 | 3 | 0 |
| (19) | 600 | 5 | 5 | 5 | 0 |
|  | 300 | 4–5 | 4 | 4 | 0 |
|  | 150 | 4 | 3–4 | 3–4 | 0 |
| (20) | 600 | 5 | 5 | 5 | 0 |
|  | 300 | 5 | 4–5 | 4 | 0 |
|  | 150 | 4–5 | 4 | 3–4 | 0 |
| (21) | 600 | 5 | 5 | 5 | 0 |
|  | 300 | 4–5 | 4 | 4 | 0 |
|  | 150 | 4 | 3–4 | 3–4 | 0 |
| (22) | 600 | 5 | 5 | 5 | 0 |
|  | 300 | 4 | 4 | 4 | 0 |
|  | 150 | 3 | 3 | 3–4 | 0 |
| (23) | 600 | 5 | 5 | 5 | 0 |
|  | 300 | 4 | 4 | 4 | 0 |
|  | 150 | 3 | 3 | 3 | 0 |
| (24) | 600 | 5 | 5 | 5 | 0 |
|  | 300 | 4 | 4 | 4 | 0 |
|  | 150 | 3–4 | 3 | 3 | 0 |
| A (Comparison, French pat. 1328112) | 600 | 5 | 5 | 4–5 | 2–3 |
|  | 300 | 4–5 | 4 | 4 | 1 |
|  | 150 | 2–3 | 2 | 3 | 0 |
| PCP (Commercial available comparison) | 800 | 0 | 0 | 3 | 0 |
|  | 600 | 0 | 0 | 0 | 0 |
| Untreated plot (control) | — | 0 | 0 | 0 | 0 |

1. Compound Nos. in the table are the same as in the preparation Example and Table 1.
2. ECHC, ELOA and Broad-leaved weed were the same as in Table 2.
3. A: Benzyl-N,N-diethylthiolcarbamate,
4. PCP: Pentachlorophenol.

EXAMPLE C.

Soil-treating test for various kinds of plants.

Test method:

Seeds of the plants to be used were sown in a pot (20–30 cm), and after 24 hours the same preparation as in Example A was sprayed on the pot at a dosage of 20, 10, 5, 2.5, or 1.25kg of the active compound per hectare. The damage degree of the plants was determined after 3 weeks according to the following scale.

0: no effect
1: slight damage or delay in growth
2: marked damage or inhibition of growth
3: heavy damage and only deficient development or only 50% emerged
4: plants partially destroyed after germination or only 25% emerged
5. plants dead or not emerged.

The active compounds, the amounts applied and the results obtained can be seen from the following Table 4.

Table 4

Test results

| Active compd. | Concentration of the active compd. (kg/hectare) | a | b | c | d | e | f | g | h | i | j | k | l |
|---|---|---|---|---|---|---|---|---|---|---|---|---|---|
| (5) | 20 | 4 | 4 | 4 | 4 | 4 | 4 | 5 | 5 | 5 | 5 | 5 | 5 |
|  | 10 | 1–2 | 2 | 1–2 | 2 | 2 | 2 | 5 | 5 | 5 | 5 | 5 | 5 |
|  | 5 | 0 | 0 | 0 | 0 | 0 | 0 | 5 | 5 | 5 | 5 | 5 | 5 |
|  | 2.5 | 0 | 0 | 0 | 0 | 0 | 0 | 5 | 5 | 5 | 5 | 5 | 5 |
|  | 1.25 | 0 | 0 | 0 | 0 | 0 | 0 | 5 | 4–5 | 4–5 | 4 | 4–5 | 4–5 |
| A (Comparison) | 20 | 5 | 5 | 5 | 5 | 5 | 5 | 5 | 5 | 5 | 5 | 5 | 5 |
|  | 10 | 1–2 | 2 | 3 | 2 | 2 | 1–2 | 5 | 5 | 5 | 5 | 5 | 5 |
|  | 5 | 0 | 0 | 0 | 0 | 0 | 0 | 4 | 5 | 5 | 5 | 5 | 5 |
|  | 2.5 | 0 | 0 | 0 | 0 | 0 | 0 | 3 | 4 | 4 | 4 | 4 | 3 |
|  | 1.25 | 0 | 0 | 0 | 0 | 0 | 0 | 2 | 2 | 2 | 2 | 2 | 2 |

Notes to Table 4:

Table 4-continued

Test results 1. (5): 2,5-dimethylbenzyl-N,N-hexamethylenethiolcarbamate
2. A: benzyl-N,N-diethylthiolcarbamate (French Pat. No. 1,328,112)
3. 
   - a: wheat;
   - b: barley;
   - c: rice plant;
   - d: cotton;
   - e: maize;
   - f: cabbage;
   - g: barnyard grass; (Echinochloa)
   - h: common purslane; (Portulacea)
   - i: goosefoot; (Chenopodium)
   - j: Shickweed; (Stellaria)
   - k: wild-amaranth (Amaranthis)
   - l: finger-grass (Digitaria)

It will be understood that the specification and examples are illustrative but not limitative of the present invention and that other embodiments with the spirit and scope of the invention will suggest themselves to those skilled in the art.

What is claimed is:

1. Thiolcarbamic acid ester compound of the formula

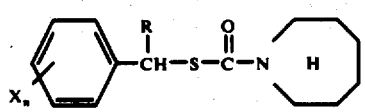

wherein
X is lower alkyl, lower alkoxy or halogen;
R is hydrogen or methyl; and
n is an integer from 0 to 3;
with the proviso that when R is hydrogen, n is an integer of from 1 to 3 and at last one X is alkyl or alkoxy.

2. Compound as claimed in claim 1 wherein X is alkyl of from 1 to 4 carbon atoms.

3. Compound as claimed in claim 1 wherein X is alkoxy of from 1 to 3 carbon atoms.

4. Compound as claimed in claim 1 wherein X is halogen.

5. Compound as claimed in claim 1 wherein R is methyl.

6. Compound as claimed in claim 1 wherein R is hydrogen, n is an integer from 1 to 3, and at least one X is alkyl or alkoxy.

7. Compound as claimed in claim 1 wherein R is hydrogen, n is 2 to 3 and at least one X is alkyl or alkoxy.

8. Compound as claimed in claim 1 designated 4-methylbenzyl N,N-hexamethylenethiolcarbamate.

9. Compound as claimed in claim 1 designated 4-isopropylbenzyl N,N-hexamethylenethiolcarbamate.

10. Compound as claimed in claim 1 designated 2,5-dimethylbenzyl N,N-hexamethylenethiolcarbamate.

11. Compound as claimed in claim 1 designated 4-methoxybenzyl N,N-hexamethylenethiolcarbamate.

12. Compound as claimed in claim 1 designated 3-chloro-4-methoxybenzyl N,N-hexamethylenethiolcarbamate.

13. Compound as claimed in claim 1 designated 3-chloro-4-ispropoxybenzyl N,N-hexamethylenethiolcarbamate.

14. Compound as claimed in claim 1 designated 2-methoxy-5-bromobenzyl N,N-hexamethylenethiolcarbamate.

15. Compound as claimed in claim 1 designated 3-methyl-4-isopropoxybenzyl N,N-hexamethylenethiolcarbamate.

16. Compound as claimed in claim 1 designated 3,5-dichloro-4-methoxybenzyl N,N-hexamethylenethiolcarbamate.

17. Compound as claimed in claim 1 designated α-methylbenzyl N,N-hexamethylenethiolcarbamate.

18. Compound as claimed in claim 1 designated α-methyl-4-chlorobenzyl N,N-hexamethylenethiolcarbamate.

19. Compound as claimed in claim 1 designated α-methyl-4-methoxybenzyl N,N-hexamethylenethiolcarbamate.

20. Compound as claimed in claim 1 designated 3,4-dimethylbenzyl N,N-hexamethylenethiolcarbamate.

21. Compound as claimed in claim 1 designated 2-methoxy-5-chlorobenzyl-N,N-hexamethylenethiolcarbamate.

22. Compound as claimed in claim 1 designated 2-methoxy-5-methylbenzyl-N,N-hexamethylenethiolcarbamate.

23. Compound as claimed in claim 1 designated 4-isopropoxybenzyl-N,N-hexamethylenethiolcarbamate.

* * * * *